United States Patent [19]

Bartley

[11] Patent Number: 4,677,234

[45] Date of Patent: Jun. 30, 1987

[54] PROCESS FOR THE PREPARATION OF ETHYLENE GLYCOL

[75] Inventor: William J. Bartley, Charleston, W. Va.

[73] Assignee: Union Carbide Corporation, Danbury, Conn.

[21] Appl. No.: 697,928

[22] Filed: Feb. 4, 1985

[51] Int. Cl.$^4$ ..................... C07C 29/136; C07C 31/20
[52] U.S. Cl. .................................... 568/864; 502/345
[58] Field of Search ........................ 568/864, 881, 885

[56] References Cited

FOREIGN PATENT DOCUMENTS 1371723 10/1974 United Kingdom .

*Primary Examiner*—J. E. Evans
*Attorney, Agent, or Firm*—Steven T. Trinker

[57] ABSTRACT

A process for the preparation of ethylene glycol by the vapor phase catalytic hydrogenation of at least one of di(lower alkyl) oxalate and lower alkyl glycolate in the presence of a hydrogenation catalyst comprising a carrier, which catalyst is suitable for the hydrogenation of alkyl oxalate and alkyl glycolate to ethylene glycol, wherein the improvement lies in preparing the catalyst by contacting the carrier with a cooper ammonium carbonate complex medium and reducing the catalytically-active copper moiety to its active copper form.

12 Claims, No Drawings

PROCESS FOR THE PREPARATION OF ETHYLENE GLYCOL

This invention relates to an improved process for the preparation of ethylene glycol by the vapor phase catalytic hydrogenation of at least one of di(lower alkyl)oxalate and alkyl glycolate in the presence of a hydrogenation catalyst comprising a carrier, which catalyst is suitable for the hydrogenation of alkyl oxalate and alkyl glycolate to ethylene glycol. More particularly, this invention relates to the catalytic hydrogenation of di(lower alkyl)oxalate to ethylene glycol using catalysts comprising carriers prepared by contacting the carrier with a copper ammonium carbonate complex and reducing the catalytically-active copper moiety to its active copper form.

INTRODUCTON TO ETHYLENE GLYCOL

Ethylene glycol is a valuable commercial chemical and finds application in deicing fluids, antifreeze, hydraulic fluids, manufacture of alkyd resins, solvents and the manufacture of polyesters. As disclosed in Kirk-Othmer, Encyclopedia of Chemical Technology, 3rd Edition, ethylene glycol is commercially made by the hydrolysis of ethylene oxide which in turn is made by the catalytic epoxidation of ethylene using air or oxygen. However, several problems, particularly raw material supply, are associated with these commercial processes.

First, ethylene is made commercially from natural gas liquids or naphthas. Second, in the catalytic epoxidation of ethylene in commercial facilities, the selectivity to ethylene oxide is usually less than 80 percent, with carbon dioxide being the primary by-product. Finally, the hydrolysis of ethylene oxide to ethylene glycol in conventional processes coproduces diethylene glycol and triethylene glycol.

It has been proposed to use synthesis gas, i.e., mixtures of carbon monoxide and hydrogen, as alternative starting materials for the preparation of ethylene glycol, thus reducing dependency on ethylene and, in turn, the feed stocks required to produce ethylene. In some of these processes, the synthesis gas is reacted to form di(alkyl)oxalates which are then hydrogenated to form the desired ethylene glycol. This hydrogenation is especially difficult since the hydrogenation must be sufficient to reduce the ester radical, yet avoid over hydrogenation of glycol and/or intermediate glycolates to ethanol and other by-products. Moreover, it can be readily appreciated that hydrogenation reactions can yield a spectrum of products, due to both under and over hydrogenation. These by-products not only reduce the efficiency to ethylene glycol, but also can present troublesome impurities that must be removed from the ethylene glycol.

U.S. Pat. No. 4,112,245 to Zehner, et al., discloses the preparation of ethylene glycol by the vapor phase catalytic hydrogenation of a dialkyl oxalate in the presence of a copper-containing catalyst. However, this patent does not disclose any significance to the carrier material nor to the impregnating medium. In particular, no significance is given to a copper ammonium carbonate complex impregnation treatment.

INTRODUCTION TO IMPREGNATED CATALYSTS

It is often desired to employ catalysts that comprise carriers. Among the benefits that are provided by catalyst carriers are reducing the amount of the catalytically-active species required, providing the catalyst in a more easily handled form, and facilitating the use of the catalyst in commercial-sized reactors without, for example, undue pressure drops or poor distribution of reactants throughout the reaction bed. Additionally, several benefits are provided by utilizing an impregnating treatment. These include more effective utilization of the catalytically-active moiety and the use of preformed carriers, which permits a wider range of carrier physical properties over such methods as pelletizing.

Impregnating solutes and media can vary widely. Moreover, with many reactions the nature of the impregnating solute and medium can affect the performance of the catalyst. The selection of suitable impregnating solutes and media has thus proven to be an empirical and complex task.

For instance, U.S. Pat. No. 2,696,475 discloses that the steps used in preparing a catalyst greatly affect the activity of the finished catalyst. The patent discloses that in preparing nickel, as well as copper, catalysts, carbonates appear to be especially desirable for obtaining a more finely divided catalyst, since their decomposition by heating leaves an oxide or metal which is in a finer state of division than oxides or metals prepared from other salts. However, the only process disclosed that benefits from such catalyst preparation is the conversion (hydrogenation) of hydrocarbons. The patent does not disclose the production of glycolic compounds by the hydrogenation of di(lower alkyl)oxalates.

British Patent Specification No. 926,235 discloses hydrogenation catalysts obtained by dissolving a metal, such as copper, in a solution of $NH_4OH$, $(NH_4)_2CO_3$ and water, while sparging in air. An amine carbonate complex of the metal is formed, which is precipitated in situ onto a carrier by heating to drive off ammonia. The carbonate/carrier mixture is fired to give the corresponding oxide and then reduced. Processes such as the hydrogenation of organic compounds, in particular the hydrogenation of double bonds in unsaturated fats and oils, are disclosed. The production of ethylene glycol is not disclosed.

British Patent Specification No. 1,371,723 discloses the preparation of a crystalline copper aluminum oxide catalytic structure by a process in which ammonia is added to copper oxide, hydroxide or salt (such as acetate, nitrate or carbonate) and the resulting solution is combined with aluminum in the form of aluminate. The patent discloses that such catalysts are useful in processes, such as the dehydrogenation of low molecular weight paraffins to olefins. However, these reactions involve chemical reactions and reaction conditions which are significantly different from those employed in the production of ethylene glycol, such as ethylene glycol by the hydrogenation of di(lower alkyl)oxalates.

Thus, while the prior art has, in general terms, recognized the importance of the impregnating solute and medium, no guidance has been provided toward selecting advantageous catalysts for the hydrogenation of di(lower alkyl)oxalates to prepare ethylene glycol.

SUMMARY OF THE INVENTION

This invention relates to a process for the preparation of ethylene glycol comprising the steps of contacting, in the vapor phase and under glycol-forming conditions, hydrogen with at least one of di(lower alkyl)oxalate and lower alkyl glycolate in the presence of a catalytically-effective amount of a copper-containing hydrogenation catalyst comprising a carrier, which catalyst is suitable for the hydrogenation of alkyl oxalate and alkyl glycolate to ethylene glycol, wherein the copper-containing catalyst is prepared by contacting the carrier with an aqueous copper ammonium carbonate complex medium and reducing the catalytically-active copper moiety to its active copper form.

Aspects of this invention relate to a copper-containing hydrogenation catalyst comprising a carrier, which catalyst is suitable for the hydrogenation of alkyl oxalate and alkyl glycolate to ethylene glycol, wherein the catalyst is prepared by contacting the carrier with a copper ammonium carbonate complex medium and reducing the catalytically-active copper moiety to its active copper form.

It has been found that catalytic hydrogenations using supported catalyst compositions prepared by the aforementioned impregnation method yield improved activity in producing ethylene glycol without adversely affecting the ethylene glycol selectivity as compared to those prepared by other impregnation methods, i.e., other solutes and other impregnating media.

In accordance with advantageous embodiments of this invention, the aforementioned copper ammonium carbonate complex impregnation treatment yields copper particles having small average diameters deposited on the carrier material. These copper particles are generally smaller in average diameter than the copper particles of catalysts prepared by impregnation with other precursors and/or other solution media and is believed to provide an increase in hydrogenation activity.

This invention also offers a convenient and efficient method of preparing copper catalysts comprising carrier material. Concentrated copper solutions can be prepared, with the impregnating treatment yielding a 10–20% copper catalyst loading after only one impregnating treatment.

DISCUSSION OF THE HYDROGENATION PROCESS

Ethylene glycol can be prepared by the vapor phase catalytic hydrogenation of a di(lower alkyl)ester of oxalic acid at elevated temperature and pressure.

An overall equation for the reaction is believed to be represented as follows:

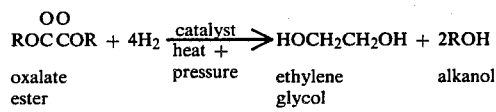

$$\underset{\text{oxalate ester}}{\text{ROOCCOOR}} + 4H_2 \xrightarrow[\text{heat + pressure}]{\text{catalyst}} \underset{\text{ethylene glycol}}{HOCH_2CH_2OH} + \underset{\text{alkanol}}{2ROH}$$

The hydrogenation of di(alkyl)oxalates is believed to proceed stepwise according to the following equations:

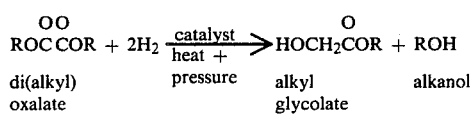

$$\underset{\text{di(alkyl) oxalate}}{\text{ROOCCOOR}} + 2H_2 \xrightarrow[\text{heat + pressure}]{\text{catalyst}} \underset{\text{alkyl glycolate}}{HOCH_2COR} + \underset{\text{alkanol}}{ROH}$$

-continued

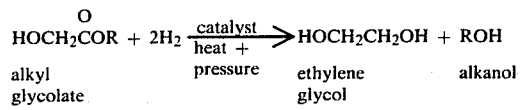

$$\underset{\text{alkyl glycolate}}{HOCH_2COR} + 2H_2 \xrightarrow[\text{heat + pressure}]{\text{catalyst}} \underset{\text{ethylene glycol}}{HOCH_2CH_2OH} + \underset{\text{alkanol}}{ROH}$$

The first step involves the hydrogenation of one of the alkoxycarbonyl groups of a di(alkyl)oxalate to form an alkyl glycolate and the corresponding alkanol. In the second step, the remaining alkoxycarbonyl group is hydrogenated to produce ethylene glycol plus the corresponding alkanol.

The oxalate esters which may be hydrogenated in accordance with the processes of this invention conform to the general formula:

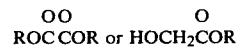

$$ROOCCOR \text{ or } HOCH_2COR$$

wherein R is a lower alkyl group. The preferred esters for use in the hydrogenation process for the preparation of ethylene glycol are those esters wherein R is an alkyl group containing from 1 to 4 carbon atoms. Especially preferred are dimethyl oxalate and diethyl oxalate.

In carrying out the hydrogenation reaction, the di(lower alkyl)ester of oxalic acid is generally preheated and vaporized, with the conditions of the hydrogenation being selected to ensure that essentially all of the ester is in the vapor state when passed over the catalyst bed. Thus, the reaction zone is maintained at an elevated temperature and pressure sufficient for hydrogenation to ethylene glycol and for preventing condensation of the oxalate ester and the product ethylene glycol.

The processes, in accordance with the present invention, are carried out by passing vaporized oxalate ester, together with hydrogen, over the catalyst maintained at a reaction zone temperature typically between about 150° C. and about 300° C. and preferably between about 180° C. and about 240° C. The molar ratio of hydrogen to oxalate ester passed to the reaction zone is usually at least sufficient on a stoichiometric basis for complete hydrogenation of the oxalate ester to ethylene glycol and is often between about 4:1 and 200:1 and preferably between about 10:1 and 100:1. A hydrogen pressure between about 1 bar and about 350 bars is frequently used and preferably the hydrogen pressure is between about 10 bars and about 100 bars. In advantageous aspects of the processes, the gas hourly space velocity (the total volume of the vaporous oxalate and hydrogen gaseous mixture, as calculated at ambient temperature and pressure, passed over a unit volume of hydrogenation catalyst bed per hour) is betwen about 2,000 hr.$^{-1}$ and about 25,000 hr.$^{-1}$ and preferably between about 5,000 hr.$^{-1}$ and about 15,000 hr.$^{-1}$. The liquid hourly space velocity of oxalate ester (calculated as the liquid volume of oxalate, expressed in liquid form per unit volume of hydrogenation catalyst which is passed over the catalyst) is typically maintained between about 0.1 hr.$^{-1}$ and about 3.0 hr.$^{-1}$ and preferably between about 0.5 hr.$^{-1}$ and about 2.0 hr.$^{-1}$. For convenience, as used herein, the oxalate liquid hourly space velocity is calculated prior to mixing with hydrogen and is based on a liquid rather than a gaseous volume.

In particularly attractive aspects of this invention, the percent conversion, calculated as the moles of oxalate in the feed minus the moles of oxalate recovered in the feed mixture after reaction divided by the moles of oxalate in the feed multiplied by 100, is maintained at greater than about 80% and preferably greater than about 95%. The percent conversion is a dependent variable, as the reaction temperature, the liquid hourly space velocity and other reaction variables are provided at sufficient interrelated values to obtain the desired conversion percent.

Angstroms, and a value of zero if said carrier has less than about 20% of its pore volume associated with pores having a diameter of at least about 1000 Angstroms.

TABLE 1

| | | PHYSICAL PROPERTIES - COMMERCIAL SILICA CARRIERS (a) | | | | |
|---|---|---|---|---|---|---|
| SUPPLIER | SUPPLIER'S IDENTIFICATION | CARRIER PARTICLE SIZE, (mm) | SURFACE AREA, (m$^2$/g) | AVERAGE PORE DIAMETER, (A°) | CRUSH STRENGTH (lbs.) | PORE VOLUME (cc/g) |
| Calsicat | silica 300 | 4.8 × 4.8 | 100 | 300 | 13 | 0.76 |
| Calsicat | silica 7000 | 4.8 × 4.8 | 3 | 7000 | 16 | 0.50 |
| Davison | Grade 59 | 2.4 − 6.4 | 300 | 95 | (d) | 1.20 |
| Davison | SMR 7-6245-2 | 4.8 × 4.8 | 128 | 193 | 25 | 0.62 |
| Davison | SMR 7-6204-2 | 7.9 × 7.9 | 96 | 220 | 28 | 0.63 |
| Davison | SMR 7-6204-1 | 4.8 × 4.8 | 155 | 130 | 20 | 0.68 |
| Davison | SMR 7-6230-1 | 4.8 × 4.8 | 245 | 90 | 20 | 0.62 |
| Davison | Grade 952 (b) | 1-2 | 300 | 120 | (d) | 1.65 |
| Calsicat | E-361D | 3.2 × 3.2 | 20 | 700 | 17 | 0.69 |
| Cabosil | M-5 (b) | 1-2 | 200 | NA(c) | (d) | NA(c) |
| United Catalysts | T-869 | 3.2 × 3.2 | 68 | 1700 | 8 | 0.43 |
| Norton | HSA 15869 | 4.8 × 4.8 | 230 | 207 | 7 | 1.20 |

(a) as found by applicant.
(b) supplied as powder, pelleted by applicant
(c) NA = Not applicable.
(d) very low

CATALYST AND ITS PREPARATION

Carriers are usually porous substances on which the catalytically-active component is deposited. Most preferably, the carriers are substantially inactive or inert. Suitable carriers may comprise one or more of silica, alumina, titania, molecular sieves, diatomaceous earth, activated carbon, silicon carbide, pumice, zeolite and the like. The silica, titania and alumina carriers are preferred, and the silica carrier is especially preferred.

The physical properties of commercially available silica carriers vary considerably. Examples, along with their physical properties, of silica carriers used in the examples herein and otherwise are given in Table 1 below. The physical characteristics of the carrier may have a substantial effect on the catalytic hydrogenation. Co-pending U.S. application Ser. No. 697,926, filed on even date herewith by W. J. Bartley, which is herein incorporated by reference, describes a process for the preparation of ethylene glycol wherein the carrier is characterized by a relative activity index of at least about 1.0, said relative activity index being defined by the formula, relative activity index = 1.38 + 0.39a + 0.76b + 0.001c + 0.35d − 0.39ab + 0.012bc + 0.003cd, wherein a is defined as the nominal external surface area of a typical carrier particle (S), expressed in square millimeters per particle units, divided by the volume (V) of the same carrier particle, expressed in cubic millimeters per particle units, minus 1.96 ((S/V) − 1.96); b is defined as the pore volume (P) of the carrier, expressed in cc/gram units, minus 0.84 (P − 0.84); c is defined as the average pore diameter (D), expressed in Angstrom units, minus 169 (D − 169); and d is defined as the macroporosity variable (M) minus 0.24 (M − 0.24), wherein the macroporosity variable is assigned a value of 1.0 if said carrier has at least about 20% of its pore volume associated with pores having a diameter of at least about 1000

Preparation of the supported catalyst, in accordance with this invention, typically involves several steps: (1) washing the carrier, (2) impregnating/coating the precursor(s) of the catalytically-active moieties on the carrier, (3) drying and/or calcining the impregnated carrier and (4) reducing the precursor of the catalytically-active moiety to its active form.

Frequently, it is desirable to pretreat the carrier, e.g., by washing, to remove significant amounts of extraneous leachable components that may be deleterious to the performance of the catalyst. Conveniently, the washing may be with an acid solution. Any suitable acid treatment (washing) technique may be utilized. An especially preferred acid for the treatment is oxalic acid. Variations of this treatment may be used to accomplish this purpose. The washing is generally sufficient to enhance the performance of the catalyst. It is thought that the washing effects the removal of at least a portion of the leachable iron and/or sulfur from the carrier. See, for example, co-pending U.S. application Ser. No. 697,927, filed on even date herewith by W. J. Bartley, which is herein incorporated by reference. That application describes a hydrogenation process for the preparation of ethylene glycol from oxalate ester, in which the carrier has a leachable iron ($Fe^{+2}$ and/or $Fe^{+3}$) content not greater than about 0.03%.

In accordance with this invention, the catalyst is typically prepared by impregnating a carrier with a medium containing a catalyst precursor which is decomposable to the catalytically-active moiety. The impregnating medium comprises a copper ammonium carbonate complex, $Cu(NH_4)_xCO_3$, wherein x is an integer from 1 to 6, typically 4. Upon drying, a substantial portion of the ammonia is driven off. Cupric carbonate (basic) is decomposed to copper oxide by calcining at an elevated temperature, and then reduced to the desired active material, copper.

Cupric carbonate (basic) is typically dissolved in an ammonium hydroxide medium to form the copper ammonium carbonate complex. The volume of $NH_4OH$ is calculated to give at least a 4 to 1 molar ratio of ammonia to copper. The maximum molar ratio is dictated by economic considerations.

The ultimate concentration of $CuCO_3$ to $NH_4OH$ depends upon the copper concentration desired in the finished catalyst and the pore volume of the carrier material. The amount of catalytically-active moiety, based on total weight of the catalyst, is generally from 1 to 50%, while a range of 2 to 20% is preferred, and about 5 to 15% being more preferred. Heating is frequently necessary to fully dissolve the complex, particularly at higher copper concentrations. Prolonged heating, if necessary, frequently results in partial decomposition of the $CuCO_3$ (basic) to $CuO$. This decomposition can be typically eliminated and the solubility of copper carbonate significantly increased by the additional step of adding ammonium carbonate, $(NH_4)_2CO_3$, to the copper carbonate prior to dissolution in ammonium hydroxide. When the system is so modified, the formation of copper oxide precipitate is greatly minimized. A $(NH_4)_2CO_3$ to $CuCO_3$ mole ratio of at least about 1:1 can be utilized, with higher ratios being preferred. The upper limit is dictated by economic considerations.

After impregnation, the carrier with deposited catalytically-active moiety or precursor, the copper ammonium carbonate complex, can be dried and the copper carbonate (decomposable catalyst precursor) converted to copper oxide. Usually, drying and decomposition are separate operations, since copper carbonate will not be decomposed under normal drying conditions. Drying typically can be accomplished by exposure to drying conditions including elevated temperatures ranging from about 50° C. to about 200° C., e.g., 0.5 to 30 hours, with temperatures ranging from about 75° C. to about 200° C. being preferred.

Calcination involves high temperature heating under oxidizing conditions so that the carbonate is decomposed and the volatile material is expelled. Calcination in an air atmosphere is a preferred means of converting the decomposable precursor to the oxide of the metal. Copper carbonate begins to decompose at a temperature of about 200° C., although this value may vary somewhat in the presence of carrier material. In general, calcination desirably is carried out by exposure to temperatures ranging from about 200° C. to about 500° C. for a time sufficient to allow substantial conversion of copper carbonate to copper oxide, with temperatures in the range of about 200° C. to about 400° C. being preferred.

The catalytically-active moiety may then be reduced to the active metal form by treatment with hydrogen prior to hydrogenation or during the hydrogenation reaction. Other reducing agents, e.g., carbon monoxide and metal hydrides, can also by employed. Reduction prior to the hydrogenation reaction typically involves purging the catalyst with an inert gas to remove oxygen then converting to the metal in the presence of a reducing agent at elevated temperatures.

Hydrogen reductions of copper oxide to copper metal are typically carried out at temperatures ranging from about 100° C. to about 300° C. with hydrogen partial pressures ranging from about 0.001 to about 100 bars in the substantial absence of oxygen. A slow reduction time is preferred and therefore preferred temperatures range from about 150° C. to about 250° C. with preferred hydrogen partial pressures ranging from about 0.01 to about 10 bars.

The following examples are provided to illustrate the present invention in accordance with the principles of this invention, but are not to be construed as limiting the invention.

EXAMPLES

The following discloses the general method employed to prepare and evaluate the catalysts designated in the examples.

1. Preparation of Supported Catalysts

The carriers are washed by slowly and continuously passing a mixture of oxalic acid, glycerine, and water in proportions of 1:1.5:1.1 by weight, respectively, through a loosely packed bed of carriers contained within a glass column which drains through a stopcock at its base. The glycerine is used to elevate the boiling point of the oxalic acid solution. The contents of the column are maintained at about 90° C. About 10-20 volumes of the solution containing oxalic acid are used to wash one volume of carrier (loosely packed volume) over a five to fifteen-hour period. The carrier material is then washed with about 20-30 volumes of distilled water at about 90° C. over a period of about five to fifteen hours and then dried overnight at about 110°-150° C. in a drying oven.

The carriers are then impregnated. The desired quantities of copper precursor, $CuCO_3$ (basic), calculated to yield a 10% copper concentration in the finished catalyst, are dissolved in an aqueous $NH_4OH$ medium. The volume of $NH_4OH$ is selected to at least fill the pores and to provide a 4 to 1 molar ratio of ammonia to copper. This mixture is allowed to stand at room temperature (about 20° C.) with occasional stirring until most of the solids are dissolved (about 1 to 60 minutes). Heating to 40°-50° C. may be required to dissolve all solids when high copper concentrations are employed.

The carrier is then placed in a vacuum flask. The top of the flask is sealed with a rubber septum, and the flask is evacuated through the side arm. A syringe needle is then used to inject the impregnating solution onto the evacuated carrier material. When the addition is complete, the material is mixed well, then the impregnated carrier is allowed to stand with occasional stirring at ambient pressure (about 1 atmosphere) for approximately 30 minutes at room temperature. It is then dried in a nitrogen atmosphere using the following heat sequence: 85° C. (for 1 hr.); 110° C. (for 2 hrs.); and 150° C. (for 2 hrs.). The impregnated carrier is then calcined at 300° C. for 2 hrs. in an air atmosphere.

To achieve reduction of the copper component, the dried, impregnated carrier is placed in the reactor used for the production of ethylene glycol and heated to 150° C. for 1 hour under flowing nitrogen. Hydrogen is then introduced into the nitrogen stream at a flow rate sufficient to give an atmosphere of about 1-2% hydrogen and a total hydrogen and nitrogen space velocity of about 2000-3000 hr.$^{-1}$ (based on the volume of the catalyst bed). The temperature is increased gradually from 150° C. to 225° C. over an 18-hour period (approximately a 4° C. increase per hour) and then held at 225° C. for 6 hours.

The additional step of adding ammonium carbonate, $(NH_4)_2CO_3$, to the copper ammonium carbonate complex may be employed to avoid the formation, if any, of copper oxide precipitate. These copper oxide solids are difficult to detect in the darkly colored impregnation mixture and are of no value from a catalyst preparation standpoint. When this additional step is utilized, the mole ratio of $(NH_4)_2CO_3$ to $CuCO_3$ is 1:1. As shown in Tables 2 through 4, cupric carbonate/ammonium hydroxide impregnating treatments employing this additional ammonium carbonate step are designated "Yes", while cupric carbonate/ammonium hydroxide treatments not employing this additional step are designated "No".

The catalysts utilized in the examples below which are representative of this invention are all prepared by essentially the same sequence of steps as described above with the following minor exceptions (identified by catalyst carrier, precursor, solution medium and letter designation as shown in Tables 2–4):

A. Calsicat 361B (3.1×3.1 mm carrier size), cupric carbonate in concentrated $NH_4OH$, prepared without the additional step of adding $(NH_4)_2CO_3$ to the cupric carbonate prior to treatment with concentrated ammonium hydroxide, deviates from the principal procedure in that no vacuum is used during the impregnation step.

B. Davison 59 (1.4–2.4 mm carrier size), cupric carbonate in concentrated $NH_4OH$, prepared without the additional step of adding $(NH_4)_2CO_3$, deviates from the principal procedure in that no vacuum is used during the impregnation step.

C. Norton HSA (4.32×4.6 mm carrier size), cupric carbonate in concentrated $NH_4OH$, deviates in that the impregnating solution used is 30% in excess of that required to fill the pores of the carrier material. The impregnation is accomplished without vacuum, and the mixture is allowed to stand 30 minutes at 30°–40° C. The excess solution is removed by vacuum filtration and the impregnated pellets are allowed to air dry in an open dish for one hour before final drying and calcining.

The catalysts utilized in the examples below which are not representative of this invention are all prepared by essentially the same sequence of steps as those catalysts representative of this invention with the following exceptions: (identified by catalyst carrier, precursor, solution medium and letter designation as shown in Tables 2–4).

D. Calcicat E361B (3.1×3.1 mm carrier size), copper nitrate in methanol, deviates from the principal procedure in that the quantity of $Cu(NO_3)_2.3H_2O$ calculated to give 10% copper in the finished catalyst is dissolved in methanol and the solution volume is adjusted to just fill the pores of the carrier material. The impregnated mixture is dried in an open dish at room temperature before final drying and calcining.

E. Norton HSA (4.32×4.6 mm carrier size), copper nitrate in an aqueous medium, deviates from the principal procedure in that the quantity of $Cu(NO_3)_2.3H_2O$ calculated to give 10% copper in the finished catalyst is dissolved in water and the impregnating solution is in 30% excess of that required to just fill the pores the carrier material. The mixture stands for 30 minutes at room temperature and is then filtered and washed one time with water. The mixture is air dried overnight at room temperature in an air purged dry box before final drying and calcining.

F. Norton HSA (4.32×4.6 mm carrier size), copper nitrate in a methanol medium, is prepared similarly to procedure E except methanol, not water, is the solvent.

G. Davison 59 (1.4–2.4 mm carrier size), copper nitrate in water, deviates from the principal procedure in that the quantity of $Cu(NO_3)_2.3H_2O$ calculated to give 10% copper in the finished catalyst is dissolved in water and the solution is adjusted to the volume required to fill the pores of the carrier material.

H. Davison 59 (1.4–2.4 mm carrier size), copper acetate in concentrated $NH_4OH$, deviates from the principal procedure in that the quantity of copper acetate calculated to give 10% copper in the finished catalyst is dissolved in a quantity of concentrated $NH_4OH$ just sufficient to fill the pores of the carrier material. The impregnated mixture is allowed to stand at room temperature for 30 minutes and is dried overnight at 110° C. in a $N_2$-purged oven. The dried material is then transferred to a 110° C. furnace and is heated to 300° C. by increasing the temperature approximately 50° C. every 30–40 minutes in air, and is held at 300° C. for 3 hours and then cooled.

I. Davison 59 (1.4–2.4 mm carrier size), copper hydroxide in concentrated $NH_4OH$, deviates from the principal procedure in that the quantity of copper hydroxide calculated to give 10% copper in the finished catalyst is dissolved in concentrated $NH_4OH$ by warming to approximately 40° C. After impregnation, the mixture is evacuated briefly and then the vacuum is released. This procedure is repeated two more times and the mixture allowed to stand at room temperature for 30 minutes prior to drying and calcining.

2. Production of Ethylene Glycol

The hydrogenation of diethyl oxalate is conducted under continuous conditions in a ¾ inch outside diameter by 16 inch stainless-steel tubular reactor (70 milliliters volume) which is coaxially fitted with a ⅛ inch diameter stainless-steel thermocouple well in accordance with the following procedure. A 20 ml charge of catalyst is dispersed with an equal volume of 3/32 inch glass helices and placed in the center of the stainless steel tube reactor with beds of 3/32 inch glass helices fully occupying the space above and below the charged catalyst. After reduction, the temperature and molecular hydrogen flow rate are then adjusted to levels set forth in Table 2 and diethyl oxalate flow is started. Liquid diethyl oxalate is premixed and vaporized with molecular hydrogen at 225° C. in a separate preheater filled with 3/32 inch glass helices and of outside dimensions identical to that of the stainless steel tubular reactor, but with an internal volume of 35 ml. The gaseous reactants are then passed downward over the catalyst bed at conditions of temperature, pressure, and gas and liquid flow rates (gas hourly space velocity and liquid hourly space velocity) as indicated in the examples in the table below. The products are then condensed and collected at reactor pressure. The condensate is analyzed by gas chromatography.

Measurement of Copper Particle Size

As shown in Tables 2 and 3, two different determinations of copper particle size are given. The copper particle size numbers not in parentheses are determined by an adaptation of the nitrous oxide decomposition method of Evans, J. W. et al., *App. Catalysis*, 7: 75 (1983). This method is as follows:

The catalyst is ground to pass a 20 mesh sieve and then placed in a ⅛-inch ID glass tube. The catalyst is reduced by a procedure similar to that used for activating the catalyst during reaction studies, namely increasing the temperature from 150° C. to 225° C. at 10° C. per hr. in 5 percent $H_2$ in $N_2$ gas and then holding at 225° C. for 5 hours. After reduction, the nitrous oxide is pulsed through the 95° C. catalyst using helium as a carrier gas. The nitrous oxide reacts with the free copper surface atoms in the catalyst forming copper oxide and liberating nitrogen. The nitrogen and nitrous oxide are then separated on a Chromosorb 101 gas chromatography column (60/80 mesh, 10 feet at 25° C.) and detected by a thermal conductivity detector. Quantitative determination of the nitrogen gas gives the amount of oxygen reacted with the free copper catalyst surface. The free copper surface area can then be determined from a stoichiometric ratio of copper to oxygen of 2.

The copper particle size numbers in parentheses under the column entitled "Cu Particle Size" in Tables 2 and 3 are determined by a known X-ray line broadening method. These determinations are for catalysts that have been used in the hydrogenation reaction, whereas the nitrous oxide determinations are for unused reduced catalysts. Of the two methods, the nitrous oxide decomposition procedure is considered to be more accurate for small particle measurement, while the x-ray method is preferred for large particle measurement.

Several impregnated catalysts on silica gels are prepared using a variety of copper precursors and/or solution media. The activities and ethylene glycol selectivities of these catalysts in the hydrogenation of diethyl oxalate to ethylene glycol are compared in Tables 2 through 4 below.

In the examples shown in Tables 2 through 4, the results of catalytic hydrogenations using catalysts prepared in accordance with this invention, by the steps of washing, impregnating with cupric carbonate precursor in an ammonium hydroxide medium (with or without the presence of $(NH_4)_2CO_3$ in the copper ammonium carbonate complex solution), drying, calcining and reducing to the active copper catalyst, are compared with those using catalysts prepared by similar methods, but with different precursors and/or solution media. The catalytic hydrogenations using catalysts prepared in accordance with this invention produced ethylene glycol at substantially increased space-time yields as compared with those catalysts prepared with different precursors and/or solution media. These increased space-time yields were accomplished with an increased or unchanged ethylene glycol selectivity, based on total products, i.e., without a sacrifice of selectivity to ethylene glycol. For example, as shown in Table 3, the catalytic hydrogenation using a catalyst prepared in accordance with this invention, i.e., the carbonate (Yes)(C) example, yields both high ethylene glycol productivity and selectivity. While, the catalytic hydrogenation using a catalyst prepared with copper nitrate in water, i.e., the second Nitrate/$H_2O$ (E) example in Table 3, yields a high ethylene glycol selectivity, but only by sacrificing ethylene glycol productivity.

In addition, as shown in Tables 2 and 3, catalysts prepared, in accordance with this invention, generally yield copper particle sizes significantly smaller than the preparations utilizing other precursors or solution media.

TABLE 2

EFFECT OF COPPER CATALYST PRECURSOR ON CATALYTIC ACTIVITY AND SELECTIVITY (1)

| CARRIER | PRECURSOR (2) | TEMP. °C. (3) | LHSV hr.$^{-1}$ (4) | GHSV hr.$^{-1}$ (5) | $H_2$/ DEO (6) | % DEO CONV. (7) | EG PROD. (8) | EG (9) SELECTIVITY | CU PARTICLE SIZE (A°) (10) |
|---|---|---|---|---|---|---|---|---|---|
| Calcicat E 361B | Carbonate (Yes) | 210 | 0.63 | 7000 | 70 | 99.8 | 3.8 | 85 | — (90) |
| Calcicat E 361B | Carbonate (No) (A) | 212 | 0.57 | 7600 | 82 | 99.8 | 3.8 | 94 | 230 (305) |
| Calcicat E 361B | Nitrate/ MeOH (D) | 212 | 0.51 | 7000 | 84 | 30 | 0.06 | 12 | 1700 (980) |
| Davison 59 | Carbonate (Yes) | 210 | 1.00 | 7650 | 47 | 100 | 6.7 | 95 | 70 (50) |
| Davison 59 | Carbonate (No) (B) | 210 | 0.92 | 7500 | 48 | 100 | 6.0 | 94 | 65 (65) |
| Davison 59 | Nitrate/$H_2O$ (G) | 221 | 0.71 | 6100 | 53 | 100 | 4.7 | 93 | 100 (60) |
| Davison 59 | Acetate/ $NH_4OH$ (H) | 210 | 0.57 | 7700 | 82 | 100 | 3.7 | 88 | 200 (220) |
| Davison 59 | Carbonate (Yes) | 210 | 1.00 | 7700 | 47 | 100 | 6.7 | 93 | 100 (60) |
| Davison 59 | $Cu(OH)_2$/ $NH_4OH$ (I) | 210 | 0.73 | 7500 | 63 | 60 | 0.4 | 13 | 300 (215) |

(1) 10% copper catalysts, 30 bars pressure
(2) See the corresponding letter designation in the "Preparation of Supported Catalysts" section
(3) Reaction zone temperature.
(4) LHSV = liquid hourly space velocity.
(5) GHSV = gas hourly space velocity.
(6) Mole ratio of hydrogen ($H_2$) to diethyl oxalate.
(7) Percent diethyl oxalate reacted.
(8) Ethylene glycol productivity (moles ethylene glycol/liter catalyst/hour).
(9) Ethylene glycol selectivity (percent ethylene glycol based on total products).
(10) See the section entitled "Measurement of Copper Particle Size".

TABLE 3

EFFECT OF COPPER CATALYST PRECURSOR ON CATALYTIC ACTIVITY AND SELECTIVITY (1)

| CARRIER | PRECURSOR (2) | TEMP., °C. (3) | LHSV, hr.$^{-1}$ (4) | GHSV, hr.$^{-1}$ (5) | $H_2$/ DEO (6) | % DEO CONV. (7) | EG PROD. (8) | EG (9) SELECTIVITY | CU PARTICLE SIZE (A°) (10) |
|---|---|---|---|---|---|---|---|---|---|
| Norton HSA | Nitrate/$H_2O$ (E) | 211 | 0.48 | 7100 | 90 | 93 | 2.2 | 72 | 560 (—) |
| Norton HSA | Nitrate/$H_2O$ (E) | 212 | 0.25 | 7000 | 172 | 99.8 | 1.5 | 90 | 560 (—) |
| Norton HSA | Carbonate (Yes) (C) | 212 | 0.90 | 7300 | 50 | 99.9 | 5.7 | 90 | 120 (75) |
| Norton HSA | Nitrate/$H_2O$ (E) | 212 | 0.49 | 7000 | 88 | 95 | 2.3 | 73 | 600 (380) |
| Norton HSA | Nitrate/ | 212 | 0.48 | 7000 | 89 | 96 | 2.4 | 75 | 830 (525) |

TABLE 3-continued
EFFECT OF COPPER CATALYST PRECURSOR ON CATALYTIC ACTIVITY AND SELECTIVITY (1)

| CARRIER | PRECURSOR (2) | TEMP., °C. (3) | LHSV, hr.$^{-1}$ (4) | GHSV, hr.$^{-1}$ (5) | H$_2$/ DEO (6) | % DEO CONV. (7) | EG PROD. (8) | EG (9) SELECTIVITY | CU PARTICLE SIZE (A°) (10) |
|---|---|---|---|---|---|---|---|---|---|
| | MeOH (F) | | | | | | | | |

(1) 10% copper catalysts, 30 bars pressure
(2) See the corresponding letter designation in the "Preparation of Supported Catalysts" section
(3) Reaction zone temperature
(4) LHSV = liquid hourly space velocity.
(5) GHSV = gas hourly space velocity.
(6) Mole ratio of hydrogen to deithyl oxalate.
(7) Percent diethyl oxalate reacted.
(8) Ethylene glycol productivity (moles ethylene glycol/liter catalyst/hour).
(9) Ethylene glycol selectivity (percent ethylene glycol based on total products).
(10) See the section entitled "Measurement of Copper Catalyst Particle Size".

TABLE 4
EFFECT OF COPPER PRECURSOR ON CATALYTIC ACTIVITY AND SELECTIVITY (1)

| Impregnating Solution (2) | Catalyst (3) Temp. (°C.) | Pressure, bars | H$_2$/ DEO (4) | GHSV, hr.$^{-1}$ (5) | LHSV, hr.$^{-1}$ (6) | % DEO CONV. (7) | EG STY (8) | EG Selectivity (9) |
|---|---|---|---|---|---|---|---|---|
| CuCO$_3$/NH$_4$OH (No) | 200 | 20 | 61 | 6900 | 0.70 | 99.8 | 285 | 93 |
| CuCO$_3$/NH$_4$OH (No) | 200 | 30 | 67 | 7500 | 0.69 | 99.9 | 279 | 97 |
| Cu(NO$_3$)$_2$/H$_2$O (G) | 200 | 30 | 51 | 5970 | 0.72 | 96.0 | 180 | 63 |

(1) All catalysts are on Davison-59 carriers (1-2 mm particle size) with a 10% copper loading.
(2) See the corresponding letter designation in the "Preparation of Supported Catalysts" section.
(3) Reaction zone temperature.
(4) Mole ratio of hydrogen (H$_2$) to diethyl oxalate.
(5) GHSV = gas hourly space velocity.
(6) LHSV = liquid hourly space velocity.
(7) Percent diethyl oxalate reacted.
(8) Ethylene glycol space-time yield (grams ethylene glycol/liter catalyst/hour).
(9) Ethylene glycol selectivity (percent ethylene glycol based on total products).

What is claimed is:

1. A process for the preparation of ethylene glycol comprising the steps of contacting, in the vapor phase, hydrogen with at least one of di(lower alkyl)oxalate and lower alkyl glycolate in the presence of a copper-containing hydrogenation catalyst comprising a carrier, which catalyst is suitable for the hydrogenation of alkyl oxalate and alkyl glycolate to ethylene glycol, wherein the copper-containing catalyst is prepared by contacting the carrier with an aqueous copper ammonium carbonate complex medium and reducing the catalytically-active copper moiety to its active copper form.

2. The process of claim 1 wherein said copper ammonium carbonate complex is prepared by contact of cupric carbonate and aqueous ammonium hydroxide.

3. The process of claim 2 wherein the molar ratio of ammonia to copper is at least about 4:1.

4. The process of claim 1 wherein said copper-containing hydrogenation catalyst comprises copper in an amount of about 1% to about 50%, by weight, based on the weight of the catalyst.

5. The process of claim 1 wherein said solid carrier comprises silica.

6. The process of claim 1 wherein the carrier is dried after contact with the aqueous copper ammonium carbonate complex medium by exposure to a temperature of about 50° C. to 200° C. for about 0.5 to 30 hours.

7. The process of claim 1 wherein the carrier is calcined after contact with the aqueous copper ammonium carbonate complex medium by exposure to a temperature of about 200° C. to 500° C.

8. The process of claim 1 wherein the catalytically-active copper moiety is reduced by hydrogen at a temperature of about 100° C. to 300° C. and with hydrogen partial pressure of about 0.001 to 100 bars.

9. The process of claim 1 wherein the pressure is between about 1 bar and 350 bars, the molar ratio of hydrogen to oxalate ester fed to the reaction zone between about 4:1 and 200:1, the temperature about 150° C. to 300° C., and the gas hourly space velocity about 2,000 hr.$^{-1}$ to 25,000 hr.$^{-1}$ and the liquid hourly space velocity about 0.1 hr.$^{-1}$ to 3.0 hr.$^{-1}$.

10. The process of claim 1 wherein said lower alkyl is methyl or ethyl.

11. The process of claim 2 wherein the copper carbonate is contacted with (NH$_4$)$_2$CO$_3$ prior to contact with ammonium hydroxide.

12. The process of claim 11 wherein the (NH$_4$)$_2$CO$_3$ to CuCO$_3$ mole ratio is at least about 1:1.

* * * * *